United States Patent [19]

Mühlegger et al.

[11] Patent Number: 4,719,097
[45] Date of Patent: Jan. 12, 1988

[54] PHOSPHATES OF RESORUFIN DERIVATIVES AND COMPOSITIONS THEREOF FOR THE DETERMINATION OF THE ACTIVITY OF PHOSPHATASES

[75] Inventors: Klaus Mühlegger; Herbert von der Eltz, both of Weilheim, Fed. Rep. of Germany

[73] Assignee: Boehringer Mannheim GmbH, Mannheim, Fed. Rep. of Germany

[21] Appl. No.: 912,395

[22] Filed: Sep. 26, 1986

[30] Foreign Application Priority Data

Oct. 1, 1985 [DE] Fed. Rep. of Germany ....... 3534927

[51] Int. Cl.$^4$ .................. A61K 31/675; C07F 9/65
[52] U.S. Cl. ........................... 424/2; 514/80; 544/73; 544/102; 424/7.1
[58] Field of Search ............... 544/73, 102; 424/2, 424/7.1; 514/80

[56] References Cited

FOREIGN PATENT DOCUMENTS 156347 3/1985 European Pat. Off. .

OTHER PUBLICATIONS

Hackh's Chemical Dictionary, McGraw-Hill (New York), 1969, p. 647.

Primary Examiner—Richard L. Raymond
Attorney, Agent, or Firm—Felfe & Lynch

[57] ABSTRACT

The present invention provides phosphates of resorufin derivatives of the general formulae:

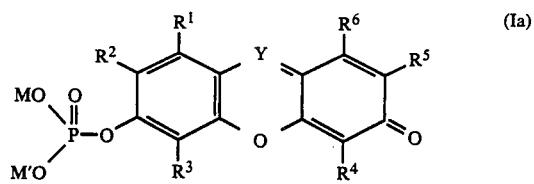

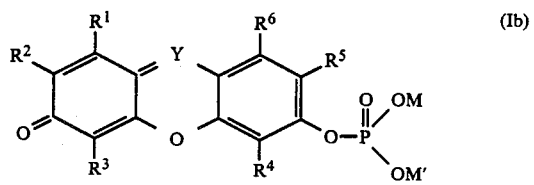

wherein $R^2$ and $R^5$, which can be the same or different, are hydrogen or halogen atoms or lower alkyl radicals, $R^1$, $R^3$, $R^4$ and $R^6$, which can be the same or different, are hydrogen or halogen atoms, cyano or carboxy groups or lower alkyl, lower alkoxy, lower alkoxycarbonyl, carboxy lower alkyl or lower alkoxycarbonyl lower alkyl radicals or carboxamide groups which are optionally mono- or disubstituted or radicals of the general formula —COO—(CH$_2$CH$_2$O)$_n$—R$^7$, R$^7$ being a hydrogen atom or a lower alkyl radical and n being a whole number of from 1 to 4, and wherein R$^6$ can additionally also be a sulphonyl or nitro group, Y is a nitrogen atom or an N→O group and M and M', which can be the same or different, are hydrogen atoms or alkali metal, alkaline earth metal or ammonium ions.

The present invention also provides processes for the preparation of these compounds and diagnostic agents containing them for the detection of phosphatases.

12 Claims, No Drawings

PHOSPHATES OF RESORUFIN DERIVATIVES AND COMPOSITIONS THEREOF FOR THE DETERMINATION OF THE ACTIVITY OF PHOSPHATASES

The present invention is concerned with phosphates of resorufin derivatives, processes for the preparation thereof and the use thereof for the determination of the activity of phosphatases.

In recent years, the determination of the activity of phosphatases has achieved importance not only in clinical chemistry but also in diagnosis. Thus, for example, alkaline phosphatase is used to an increasing extent as indicator enzyme for enzyme immunoassays. The determination of the activity of acidic phosphatase is a valuable means for the early diagnosis of carcinomas of the prostate.

For the determination, the phosphatase-containing sample is usually mixed with an appropriate substrate which is then split by the enzyme. As a rule, these substrate are orthophosphoric acid monoesters. The alcoholic component liberated after the action of the enzyme is measured. For this purpose, compounds are preferably used which can be detected spectroscopically in the visible or UV range or also fluorimetrically.

Thus, for example, in clinical analysis, 4-nitrophenyl phosphate has already been used for a long time and frequently, this being split by phosphatases to give 4-nitrophenol and phosphate. The formation of the yellow phenolate ion is achieved by the addition of alkali which, in the case of the determination of acidic phosphates, means an additional rebuffering step.

In the case of another process, 1-naphthyl phosphate is used. For visualisation, the liberated naphthol must be reacted with a diazonium salt to give an azo dyestuff (see A. Babson, Clin. Chem., 30, 1418/1984).

The determination of ezyme activities with fluorogenic substrates is widely used. The sensitivity in comparison with the photometric methods is often increased by several decimal powers. In some cases, it is necessary to work with fluorogenic substrates, for example in the case of the investigation of enzymatic activities in cells with automatic devices, for cell differentiation (cytofluorometry) or in the case of the analysis of immobilised enzymes by means of throughflow microfluorometry. In other cases, for example in the case of the determination of the enzyme labelling of test systems (enzyme immunoassays), the multiplication effect of the enzymatic catalysis is considerably strengthened by the use of fluorogenic substrates.

Previously known fluorogenic substrates for phosphatases contain as fluorophor, for example derivatives of indoxyl (see J. P. Horwitz et al., J. Med. Chem., 9, 447/1966) or of 4-methylumbelliferone (see H. N. Fernley and P. E. Walker, Biochem. J., 97, 95/1965). However, these compounds posses disadvantages for the kinetic analysis of complex systems. Thus, indoxyl derivatives, after the enzymatic splitting thereof, undergo a series of chemical changes which complicate the analysis. 4-Methylumbelliferone derivatives must be excited in the UV range, in which case the inherent fluorescene of simultaneously present biological or synthetic materials have a disturbing effect.

Therefore, there is still a need for substrates with which various phosphatases (phosphomonoester hydrolases) can be determined in a simple, quick and dependable way and which, if possible, can be used not only in photometric but also in fluorimetric determination processes. It is an object of the present invention to fulfil this task.

This problem is solved, according to the present invention, by the provision of new phosphates of resorufin derivatives which, with the help of phosphatases, can be split into the phosphate moiety and into the resorufin derivative. The latter are readily water-soluble compounds which display a readily measurable absorption in the visible spectrum and, furthermore, can easily be excited to fluorescence.

Thus, according to the present invention, there are provided phosphates of resorufin derivatives of the general formulae:

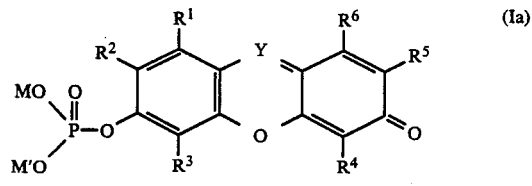
(Ia)

and

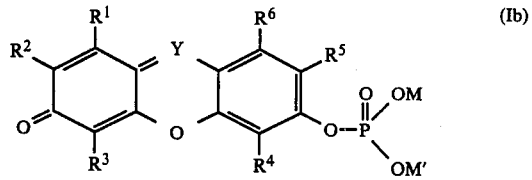
(Ib)

wherein $R^2$ and $R^5$, which can be the same or different, are hydrogen or halogen atoms or lower alkyl radicals, $R^1$, $R^3$, $R^4$ and $R^6$, which can be the same or different, are hydrogen or halogen atoms, cyano or carboxy groups or lower alkyl, lower alkoxy, lower alkoxycarbonl, carboxyl lower alkyl or lower alkoxycarbonyl lower alkyl radicals or carboxamide groups which are optionally mono- or disubstituted or radicals of the general formula $-COO-(CH_2CH_2O)_n-R^7$, $R^7$ being a hydrogen atom or a lower alkyl radical and n being a whole number of from 1 to 4, and wherein $R^6$ can additionally also be a sulpho or nitro group, Y is a nitrogen atom or an N→O group and M and M', which can be the same or different, are hydrogen atoms or alkali metal, alkaline earth metal or ammonium ions.

Phosphates of resorufin derivatives of general formulae (Ia) and (Ib) are new compounds. They can be prepared according to known methods by the phosphorylation of the phenolic function.

Preferably, resorufin derivatives of the general formulae:

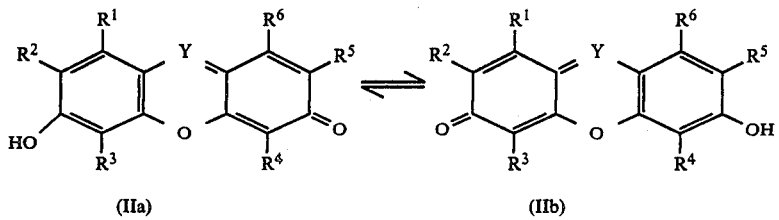

(IIa)                               (IIb)

in which $R^1$ to $R^6$ and Y have the same meanings as above, are reacted in known manner with a halide of pentavalent phosphorus, preferably in the presence of an inorganic or organic acid-binding agent, and the dihalogen phosphonyloxy compound subsequently hydrolysed.

Resorufin derivatives of general formulae (IIa) and (IIb) are the subject of European Patent Specification No. 0,156,347.

As halides of pentavalent phosphorus, there can be used, for example phosphorus oxytrichloride, phosphorus pentachloride or pyrophosphoric acid tetrachloride, the latter compound preferably being used.

As acid-binding agents, there can be used inorganic and organic bases, for example alkali metal carbonates and trialkylamines. Expecially favourable results are obtained with the use of cyclic diamines, for example diazabicycloundecene (DBU), which, by formation of corresponding ammonium salts, bring about an especially good solubility of the resorufin derivatives in the solvents and diluents used for the reaction.

As solvents and diluents, under the reaction conditions, there are especially suitable organic liquids, such as chloroform, dichloromethane and acetonitrile.

The reaction is preferably carried out in the presence of a solvent or diluent at a temperature of from $-30°$ to $+20°$ C.

The hydrolysis of the dichlorophosphonyloxy compounds formed as intermediates takes place gently at a temperature of from $0°$ to $20°$ C. by neutralisation with aqueous alkali metal carbonate solution, alkaline earth metal hydroxide solution, triethylamine or triethylammonium bicarbonate. The alkali metal, alkaline earth metal or ammonium salts obtained are concentrated in a vacuum and the desired phosphoric acid resorufin derivative monoesters are obtained therefrom by appropriate chromatographic processes. Another method consists in the precipitation of the free, relatively sparingly soluble free phosphoric acid esters from concentrated aqueous solutions of the alkali metal, alkaline earth metal or ammonium salts by acidification with mineral acids, for example hydrochloric acid.

In the case of the synthesis of phosphates of the resorufin derivatives of general formulae (IIa) and (IIb), there are obtained readily water-soluble, non-fluorescing compounds of the general formulae (Ia) and (Ib) in the form of their alkali metal or ammonium salts from which, by enzymatic splitting with the help of phosphatases, fluorescing resorufin derivatives are again liberated.

By halogen in the definition of $R^1$ to $R^7$ is to be understood fluorine, chlorine, bromine and iodine, chlorine and bromine being preferred.

The lower alkyl radicals in the definition of $R^1$ to $R^7$ contains up to 5 and preferably up to 3 carbon atoms, the methyl radical being especially preferred.

The lower alkoxy radical in the definition of $R^4$ and $R^6$ contains up to 5 and preferably up to 3 carbon atoms, the methoxy radical being especially preferred.

The lower alkoxy and lower alkyl moieties of the lower alkoxycarbonyl, carboxyl lower alkyl, as well as of the lower alkoxycarbonyl lower alkyl radicals in the definitions of $R^4$ and $R^6$ also contain up to 5 and preferably up to 3 carbon atoms, the methoxy and methyl radicals, respectively, being especially preferred.

The substituents of the carboxamido group can be alkyl, alkoxyalkyl, carboxyalkyl and alkoxycarbonylalkyl radicals, the alkyl and alkoxy moities containing up to 5 and preferably up to 3 carbon atoms. In the case of a disubstituted carboxamide function, the two substituents can be joined together to form a ring which can be interrupted by heteroatoms, for example oxygen, nitrogen and sulphur.

By alkali metal ions in the definition of M and M' are preferably to be understood lithium, sodium and potassium ions and by alkaline earth metal ions are preferably to be understood magnesium, calcium and barium ions.

Ammonium ions in the definition of M and M' can be the unsubstituted ammonium ion or ammonium ions substituted one or more times by alkyl or aralkyl radicals. By an alkyl radical is to be understood a radical containing up to 5 carbon atoms and especially a methyl or ethyl radical. The aralkyl radical is preferably the benzyl radical. The substituents in the case of substituted ammonium ions can be the same or different.

Excitement and emission of the products according to the present invention lie in the visible spectral range with sufficient quantum yield. The maximum fluorescene intensity of the resorufin is achieved at pH values above 7.0 and only decreases slowly to lower pH values. In aqueous solution, the glycosides of resorufin are mostly yellow coloured ($\lambda_{max.}$ at about 470 nm). After the enzymatic reaction, the products mostly display a red colour ($\lambda_{max.}$ at about 570 nm) so that the substances are also outstandingly useful for photometric determinations and for noninstrumental, visual processes.

The present invention also provides diagnostic agents for the determination of the activity of phosphatases which contain at least one of the new phosphates of resorufin derivatives of general formula (Ia) or (Ib).

The use of phosphates of resorufin derivatives of general formulae (Ia) and (Ib) as substrates for phosphatases gives test symtoms which are distinctly more sensitive than those previously known. The new substrates can be used with advantage for the determination of the activity of phosphatases not only in biochemical and biotechnological fields but also in clinical chemical fields. They are much more sensitive than previously known substrates. Several advantages result from this:

(a) smaller enzyme activities can be measured;
(b) smaller amounts of sample can be used;
(c) the determination of the activity can take place in a considerably shorter period of time;

(d) the small amount of sample used and the favourable wavelength also reduce the susceptability of the method to disturbances by other components of the sample; and (e) the reaction can be measured in carrier matrices with immobilised enzyme.

We have found that the substrates according to the present invention can be used for the determination of the activity of phosphatases of any origin. The diagnostic agents according to the present invention with substrates of the general formulae (Ia) and (Ib) react much more sensitively than the previously known test agents.

The phosphates of resorufin derivatives of general formulae (Ia) and (Ib) can also be used for immunological methods of determination in which phosphatases are used as indicator enzymes, the activity of which must be determined after carrying out the immunological reaction. Such immunological methods of determination with enzymatic indicator reaction are known as enzyme immunoassays. These methods serve for the determination of the concentration of proteins, polysaccharides, hormones, pharmaceuticals and other low molecular weight substances in the range of from $10^{-5}$ to $10^{-12}$ Mole/liter. Depending upon the necessity of phase separation steps, a differentiation is made between a homogeneous and heterogeneous carrying out of the test. A further subdivision can be made into competitive and non-competitive test principles.

However, all test principles work with enzyme-antigen or enzyme-antibody conjugates. The enzyme indicator reaction is common to all enzyme immunoassays. Indicator enzymes suitable for such purposes can be, for example, phosphatases. The determination of the phosphatases in such enzyme immunoassays usually takes place by adding an appropriate substrate which is split enzymatically and measured in the usual way photometrically or also fluorometrically.

Consequently, an improvement of the phosphatase test system also results in considerable advantages in such enzyme immunoassays:

1. the higher sensitivity here also makes possible a lowering of the detection limits, shorter reaction times and smaller amounts of sample and thus also lesser disturbances by other components of the sample;
2. in the case of certain reaction procedures, the more favourable measurement wavelength reduces the susceptability of the methods to disturbances by insoluble components, for example by turbidities.

Besides one or more of the substrates according to the present invention of general formulae (Ia) and (Ib), the diagnostic agent contains an appropriate buffer system, as well as possibly further appropriate additives normally used for such diagnostic agents, for example wetting agents, stabilizers and the like. The diagnostic agent can be in the form of a solution, lyophilisate, powder mixture or reagent tablet or can be applied to an absorbent carrier.

The diagnostic agent according to the present invention in the form of a solution preferably contains all reagents required for the test. As solvents, there can be used, for example, water and mixtures of water with a water-soluble organic solvent, for example methanol, ethanol, acetone or dimethylformamide. For reasons of storage stability, it can be advantageous to divide the reagents required for the test into two or more solutions which are only mixed when the actual investigation is to be carried out.

For the preparation of a diagnostic agent in the form of a lyophilisate with a total weight of from about 5 to 20 mg. and preferably of about 10 mg., a solution is dried which, besides the reagents required for the test, also contains conventional structure formers, for example polyvinylpyrrolidone, and possibly further fillers, for example mannitol, sorbitol or xylitol.

A diagnostic agent in the form of a powder mixture or reagent tablet can be produced by mixing the components of the test with conventional galenical additives and then granulating. Additives of this kind include, for example, sugar alcohols, such as mannitol, sorbitol and xylitol, or other soluble, inert compounds, for example polyethylene glycols or polyvinylpyrrolidone. The powder mixtures or reagent tablets generally have an end weight of about 30 to 200 mg. and preferably of 50 to 80 mg.

For the production of the diagnostic agent in the form of a test strip, an absorbent carrier, preferably filter paper, cellulose or synthetic resin fibre fleece, is impregnated with solutions of the necessary reagents usually employed for the production of test strips in readily volatile solvents, for example water, methanol, ethanol or acetone. This can take place in one impregnation step. However, it is often preferable to carry out the impregnation in several steps, solutions thereby being used each of which contains a part of the components of the diagnostic agent. Thus, for example, in a first step, impregnation can be carried out with an aqueous solution which contains the buffer and other water-soluble additives and then, in a second step, with a solution which contains the phosphatase substrate. The finished test papers can be used as such or can be struck in known manner on to handles or preferably sealed between synthetic resins and fine meshes according to Federal Republic of Germany Patent Specification No. 21 18 455.

The following Example, which are given for the purpose of illustrating the present invention, describe some of the numerous process variants which can be used for the synthesis of the new compounds according to the present invention, as well as, by way of example, the use of the new phosphates of resorufin derivatives for the determination of the activity of phosphatases:

EXAMPLE 1

Resorufin phosphoric acid 5 g. (23.5 mMole) resorufin are suspended in 200 ml. dichloromethane and mixed with 7.5 ml. (49.3 mMole) 1,8-diazabicyclo[5,4,0]undec-7-ene. The reaction mixture is stirred at ambient temperature until dissolving is complete and this then added dropwise, while stirring, within the course of about 1 hour, into a mixture, cooled to about $-15°$ C., of 15 ml. (95 mMole) pyrophosphoric acid chloride in 500 ml. dichloromethane.

The reaction mixture is subsequently stirred into 500 ml. of a saturated aqueous sodium hydrogen carbonate solution and mixed with additional sodium hydrogen carbonate until no further carbon dioxide formation is observed. After separation of the aqueous phase and concentration thereof in a vacuum to about 200 ml., it is adjusted to a pH value of 2.5 with 5 N hydrochloric acid. At this pH value, the free resorufin phosphoric acid precipitates out as a fine, yellow-orange coloured material. After drying in a vacuum over anhydrous calcium chloride, there are obtained 1.25 g. (18% of theory) of resorufin phosphoric acid.

Elementary analysis: $C_{12}H_8NO_6P \times H_2O$ (M.W. 311.2) calc.: C 46.3%; H 3.2%; N 4.5%; P 10.0%. found: 44.8%; 2.9%; 4.5%; 9.5%.

Electrophoretic mobility (paper, 0.05 M triethylammonium bicarbonate buffer, pH 7.5), relative to resorufin (=1): 4.5.

Rf value (TLC on Cellulose CEF, Riedel de Haen; elution agent: aqueous 1 M ammonium acetate solution-/ethanol=5:2 v/v): 0.18.

EXAMPLE 2

Resazurin phosphoric acid 251 mg. (1 mMole) Resazurin are suspended in 25 ml. dry diethyl ether and the mixture is cooled to −30° C. Within the course of about 20 minutes, 2.5 g. (10 mMole) pyrophosphoric acid chloride are added dropwise thereto, followed by stirring for a further 60 minutes in a cold bath. Subsequently, about 50 ml. diethyl ether are added to the reaction solution, a brown-yellow precipitate thereby being obtained. This is digested several times with fresh diethyl ether and then hydrolysed by the addition of ice to which 0.5 ml. triethylamine has been added.

For the separation of unreacted resazurin, the aqueous solution is applied to the ion exchanger DEAE-Sephadex A-25 in the carbonate form (20 ml. column volume) and eluted with a linear gradient of 0.5 M aqueous triethylammonium carbonate solution.

The product-containing fractions are combined, evaporated in a vacuum, the residue taken up in methanol several times and again concentrated. After finally dissolving in water and lyophilising, there are obtained 40 mg. resazurin phosphoric acid in the form of the triethylammonium salt.

Electrophoretic mobility (paper, 0.05 M triethylammonium bicarbonate buffer, pH 7.5) relative to resazurin (=1): 4.1.

Rf value (TLC on Cellulose CEF, Riedel de Haen; elution agent 1 M aqueous ammonium acetate solution-/ethanol=5:2 v/v): 0.2.

EXAMPLE 3

Resorufin-4-carboxylic acid morpholide phosphate (a) Resazurin-4-carboxylic acid 1.60 g. (10.5 mMole) Nitrosoresorcinal, 1.55 g. (10.0 mMole) 2,6-dihydroxybenzoic acid and 0.86 g. (10 mMole) pyrolusite are taken up in 20 ml. methanol and cooled to 0° C. 1.06 ml. concentrated sulphuric acid are added dropwise thereto. The reaction mixture is then further stirred for 2 hours without cooling. The precipitated red product is filtered off, washed with methanol and dried. Yield: 2.3 g. (85% of theory) resazurin-4-carboxylic acid.

UV/VIS (0.1 M potassium phosphate buffer, pH 7.5): $\lambda_{max.}=614$ nm ($\epsilon=48$ $cm^2mol^{-1}$); after acidification: $\lambda_{max.}=522$ nm ($\epsilon=32$ $cm^2mol^{-1}$).

(b) Resorufin-4-carboxylic acid 2.5 g. Resazurin-4-carboxylic acid are dissolved in 20 ml. water and 5 ml. 25% aqueous ammonia solution. 5 g. zinc dust are added, while cooling with ice, to the blue solution. Thereafter, the ice cooling is removed so that the solution gradually warms up to ambient temperature. The reduction can be recognized easily by the colour change from blue to dark violet or with the help of thin layer chromatography (elution agent: methanol-/ethyl acetate 1:1 v/v). Excess zinc powder is filtered off. The reaction solution is acidified with 5 ml. glacial acetic acid and concentrated hydrochloric acid. The precipitated product is filtered off, washed with dilute hydrochloric acid and dried in a vacuum over anhydrous calcium chloride. Yield: 1.8 g. (82% of theory) of resorufin-4-carboxylic acid.

UV/VIS: 0.1 M potassium phosphate buffer, pH 7.5): $\lambda_{max.}=579.4$ nm ($\epsilon=43.6$ $cm^2mol^{-1}$); after acidification: $\lambda_{max.}=485.9$ nm ($\epsilon=34.7$ $cm^2mol^{-1}$).

Fluorescence: absorption: $\lambda_{max.}=579$ nm; emission: $\lambda_{max.}=593$ nm.

(c) N,O,O-Triacetyldihydroresorufin-4-carboxylic acid 5 g. (19.4 mMole) Resorufin-4-carboxylic acid or 5.3 g. (19.4 mMole) resazurin-4-carboxylic acid are heated under reflux for 0.5 hours in 100 ml. 10% hydrochloric acid with 7 g. (38 mMole) stannous chloride. The solution thereby becomes green coloured. The reaction mixture is allowed to cool, the precipitated dihydroresorufin-4-carboxylic acid is filtered off under an atmosphere of nitrogen and dried in a vacuum over phosphorus pentoxide. The crude product thus obtained is heated under reflux for 30 minutes with 30 ml. acetic anhydride and 20 mg. sodium acetate. The reaction mixture is introduced into 200 ml. ice water and stirred for 14 hours. The precipitate is recrystallised from ethanol/water. There are obtained 4.8 g. (65% of theory) N,O,O-triacetyldihydroresorufin-4-carboxylic acid; m.p. 197°-199° C. Thin layer chromatography (silica gel; elution agent: chloroform/methanol/glacial acetic acid: 9:1:0.1 v/v/v): Rf=0.33.

(d) N,O,O-Triacetyldihydroresorufin-4-carboxylic acid chloride 3.85 g. (10 mMole) N,O,O-triacetyldihydroresorufin-4-carboxylic acid are mixed with 5.4 ml. (60 mMole) oxalyl chloride and cooled to −10° C. A few drops of dimethylformamide are added thereto and the reaction mixture allowed to warm to ambient temperature, while stirring. The educt thereby dissolves with the evolution of gas. After termination of the gas evolution, stirring is continued for 0.5 hours and the reaction mixture is evaporated. The residue is taken up three times with 20 ml. amounts of dry methylene chloride and then evaporated to dryness. There are thus obtained 4 g. of crude acid chloride which is further worked up without further purification.

Thin layer chromatography (silica gel; elution agent: chloroform/methanol/glacial acetic acid 9:1:0.1 v/v/v): Rf=0.42; colourless spot which becomes red coloured after a few hours.

(e) N,O,O-Triacetyldroresorufin-4-carboxylic acid morpholide 11.3 g. (31.4 mMole) of the crude acid chloride are dissolved in 150 ml. dry methylene chloride. 8.7 ml. (63 mMole) triethylamine are added dropwise thereto and subsequently 3.3 ml. (37.7 mMole) morpholine. The solution is further stirred for 2 hours, washed with 1% aqueous citric acid solution, aqueous sodium hydrogen carbonate solution and water, the organic phase is dried over anhydrous magnesium sulphate and evaporated. The residue is crystallised from ethanol. Yield 8.1 g. (63% of theory); m.p. 133°-135° C. (decomp.).

(f) Resorufin-4-carboxylic acid morpholide 3.7 g. (9 mMole) triacetyldihydroresorufin-4-carboxylic acid morpholide are taken up with 250 ml. methanol and 250 ml. water. 36 ml. 1 N aqueous sodium hydroxide solution are added thereto, as well as 6.0 g. (18 mMole) potassium ferricyanide, and the reaction mixture is stirred for 14 hours at ambient temperature. After acidification with hydrochloric acid to pH 3, the solution is evaporated to dryness and the residue is digested with acetone. The dyestuff solution is filtered over 500 ml. silica gel with acetone as elution agent. After evaporation of the dyestuff-containing eluate, there are obtained 2.3 g. (80% of theory) resorufin-4-carboxylic acid morpholide.

UV/VIS (0.1 M potassium phosphate buffer, pH 7.5): $\lambda_{max.}=575$ nm ($\epsilon=55,000$ cm$^2$ mol$^{-1}$). TLC (elution agent, see under d): Rf=0.52.

$^1$H-NMR ([D]$_6$-DMSO): $\delta=3.3-3.8$ (m, 8H); 6.50 (d, J=2 Hz, 1H); 6.64 (d, J=10 Hz, 1H); 6.76 (dd, J=10 and 2 Hz, 1H); 7.44 and 7.51 (each d, J=10 Hz, 2H).

(g) Resorufin-4-carboxylic acid morpholide phosphate

Resorufin-4-carboxylic acid morpholide phosphate is prepared analogously to Example 1 by reacting resorufin-4-carboxylic acid morpholide with pyrophosphoric acid chloride. Purification takes place by preparative high pressure liquid chromatography (HPLC) on an RP-C 13 column with an isopropanol/triethylammonium acetate gradient.

Electrophoretic mobility (paper, 0.05 M driethylammonium bicarbonate buffer, pH 7.5) relative to resorufin-4-carboxylic acid morpholide (=1): 1.9

Rf value: (TLC on Cellulose CEF, Riedel de Haen, elution agent: 1 M aqueous ammonium acetate solution-/ethanol=5:2 v/v): 0.3.

EXAMPLE 4

2,8-Dibromoresorufin phosphate

The desired product is obtained by reacting 2,8-dibromoresorufin (see G. B. Afanasieva et al., Khim, Geterotsik L. Soedin, pp. 348-353/1974) with pyrophosphoric acid chloride analogously to Example 1.

Electrophoretic mobility (paper, 0.05 M triethylammonium bicarbonate buffer, pH 7.5) relative to 2,8-dibromoresorufin (=1): 3.2.

Rf value: (TLC on Cellulose CEF Riedel de Haen, elution agent 1 M aqueous ammonium acetate solution-/ethanol=5:2 v/v): 0.28.

EXAMPLE 5

4-Methylresorufin phosphate

4-Methylresorufin 32.5 g. (0.6 mole) potassium hydroxide dissolved in 300 ml. ethanol are mixed with 50 g. (0.4 mole) 2-methyl-resorcinol and stirred until dissolving is complete. 63.5 ml. (0.43 mole) isopentyl nitrite are slowly added dropwise to the solution cooled with ice-salt in such a manner that the internal temperature does not exceed +10° C. After the dropwise addition is complete, stirring is continued in the ice bath for a further 2 hours. The separated solid material is filtered off with suction, washed with ethanol and subsequently dissolved in 270 ml. water and again precipitated by the addition of concentrated hydrochloric acid. The yellow precipitate obtained is filtered off with suction end washed with water. The product is dried in a vacuum at 50° C. over anhydrous calcium chloride. There are obtained 75 g. 4-nitroso-2-methylresorcinol.

75 g. 4-Nitroso-2-methylresorcinol and 42 g. (0.38 mole) resorcinol are dissolved in 750 ml. methanol. 36 g. manganese dioxide are added to this solution, with ice cooling. Subsequently, 43 ml. concentrated sulphuric acid are added dropwise thereto, following by stirring for 2 hours. Insoluble material is then filtered off with suction and the filtrate is concentrated to about one-third of its volume. The concentrate is stirred into 1.5 liters of water. A solid material thereby separates out. It is filtered off with suction and subsequently washed with water. The solid material is then dissolved in 750 ml. water and mixed with 180 ml. 25% aqueous attonic solution and 40 g. zinc dust. After stirring for 30 minutes, 4-methylresorufin is precipitated out with concentrated hydrochloric acid, filtered off with suction and dried in a vacuum at 50° C. over anhydrous calcium chloride. There are thus obtained 45 g. (52% of theory) of product.

Rf value (TLC on Cellulose CEF, Riedel de Haen, elution agent 1 M aqueous ammonium acetate solution-/ethanol=5:2 v/v): 0.71.

4-Methylresorufin phosphate is prepared analogously to Example 1 by reacting 4-methylresorufin with pyrophosphoric acid chloride.

Electrophoretic mobility (paper, 0.05 M triethylammonium bicarbonate buffer, pH 7.5) relative to 4-methylresorufin (=1): 3.4

Rf value (TLC on Cellulose CEF, Riedel de Haen, elution agent 1 M aqueous ammonium acetate solution-/ethanol=5:2 v/v): 0.2.

EXAMPLE 6

Determination of the activity of alkaline phosphatase

Resorufin-4-carboxylic acid morpholide phosphate is dissolved in a concentration of 1 mg./ml. in 0.1 M glycine buffer (pH 10.5). Upon adding a solution which contains alkaline phosphatase, a colour change takes place from orange-yellow to blue-violet. The intensity of the blue-violet coloration is proportional to the concentration of the alkaline phosphatase in the sample.

With the help of samples with known concentrations of alkaline phosphatase, there can be prepared a calibration curve on the basis of which the unknown alkaline phosphatase content of a sample can be determined.

EXAMPLE 7

Determination of the activity of acidic phosphatase

A chromatography paper strip is impregnated with a solution of 2,8-dibromoresorufin phosphate in a concentration of 1 mg./ml. in 0.1 M citrate buffer (pH 5.0) and dried. Upon dropping on a solution of acidic phosphatase, a colour change takes place to blue-red.

The intensity of the blue-red coloration is proportional to the concentration of the acidic phosphatase in the sample.

With the help of samples with known concentrations of acidic phosphatase, there can be produced a calibration curve on the basis of which the unknown acidic phosphatase content of a sample can be determined.

It will be understood that the specification and examples are illustrative but not limitative of the present invention and that other embodiments within the spirit and scope of the invention will suggest themselves to those skilled in the art.

What is claimed is

1. A phosphate of resorufin derivative of the formula:

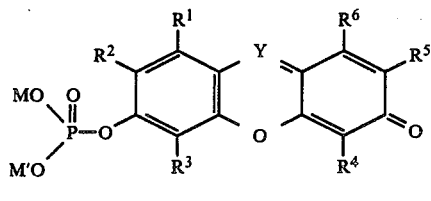

(Ia)

or

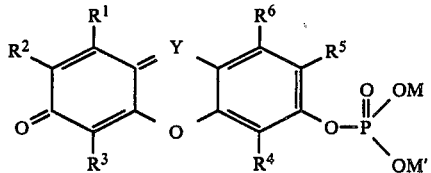

(Ib)

wherein

R² and R⁵, which can be the same or different, are hydrogen, halogen, $C_1$–$C_5$ alkyl;

R¹, R³, R⁴ and R⁶, which can be the same or different, are hydrogen, halogen, a cyano group or a carboxy group of $C_1$–$C_5$ alkyl, $C_1$–$C_5$ alkoxy, $C_1$–$C_5$ alkoxycarbonyl, carboxy-$C_1$–$C_5$-alkyl or $C_1$–$C_5$ alkoxycarbonyl-$C_1$–$C_5$alkyl, or carboxamide which is optionally mono or disubstituted with $C_1$–$C_5$ alkyl, $C_1$–$C_5$ alkoxy-$C_1$–$C_5$ alkyl, carboxy-$C_1$–$C_5$ alkyl, $C_1$–$C_5$-alkoxy-carbonyl-$C_1$–$C_5$ alkyl, or the disubstituted carboxamide optionally substituted with substituents joined together to form a ring which can be interrupted by oxygen, nitrogen or sulphur, or radicals of the formula —COO—($CH_2CH_2O$)$_n$—R⁷, R⁷ being hydrogen or $C_1$–$C_5$ alkyl and n being an integer number of from 1 to 4; and wherein R⁶ can additionally also be sulpho or nitro;

Y is a nitrogen atom or an N→O group; and

M and M', which can be the same or different, are hydrogen atoms, alkali metal, alkaline earth metal or ammonium ions said ammonium ions being optionally substituted one or more times by $C_1$–$C_5$ alkyl or aralkyl, each substituent being independently selected.

2. The phosphate of claim 1 wherein R¹, R³, R⁴ and R⁶ are individually selected from the group consisting of hydrogen, halogen, $C_1$–$C_5$ alkyl or carboxamide.

3. The phosphate of claim 1 wherein said halogen is chlorine or bromine.

4. The phosphate of claim 1 wherein said disubstituted carboxamide in R¹, R³, R⁴ or R⁶, substituted with substituents joined together to form a ring is

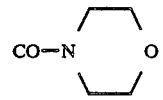

5. The phosphate of claim 1 wherein the $C_1$–$C_5$ alkyl is methyl.

6. The phosphate of claim 1 designated resorufin phosphoric acid.

7. The phosphate of claim 1 designated resazurin phosphoric acid.

8. The phosphate of claim 1 designated resorufin-4-carboxylic acid morpholide phosphate.

9. The phosphate of claim 1 designated 2,8 dibromoresorufin phosphate.

10. The phosphate of claim 1 designated 4-methylresorufin phosphate.

11. Composition for the detection of phosphatase containing at least one chromogenic and/or fluorogenic substrate and a buffer, wherein said substrate is a phosphate of claim 1.

12. Composition of claim 11 wherein said phosphate is resorufin phosphoric acid; resazurin phosphoric acid; resorufin-4-carboxylic acid morpholide phosphate; 2,8 dibromoresorufin phosphate; or 4-methylresorufin phosphate.

* * * * *

UNITED STATES PATENT AND TRADEMARK OFFICE
CERTIFICATE OF CORRECTION

PATENT NO. : 4,719,097
DATED : January 12, 1988
INVENTOR(S) : Klaus Muhlegger and Herbert von der Eltz It is certified that error appears in the above-identified patent and that said Letters Patent is hereby corrected as shown below:

Abstract, line 12: change "sulphonyl" should be -- sulpho --;

Column 1, line 24: change "substrate" to -- substrates --;

Column 8, line 12: change "N, O, Q" to -- N, O, O --;

Column 9, line 27: change "13" to -- 18 --;

Column 9, line 31: change "driethylammonium" to -- triethylammonium --.

Signed and Sealed this

Thirtieth Day of August, 1988

Attest:

DONALD J. QUIGG

Attesting Officer

Commissioner of Patents and Trademarks